United States Patent
Yamaguchi

[11] Patent Number: 5,995,778
[45] Date of Patent: Nov. 30, 1999

[54] APPARATUS AND METHOD FOR DETECTING TONER DENSITY IN A LIQUID DEVELOPER

[75] Inventor: Chiseki Yamaguchi, Niigata, Japan

[73] Assignee: NEC Corporation, Japan

[21] Appl. No.: 09/130,222

[22] Filed: Aug. 6, 1998

[30] Foreign Application Priority Data

Aug. 8, 1997 [JP] Japan ................................. 9-214455

[51] Int. Cl.$^6$ ................................................. G03G 15/10
[52] U.S. Cl. ................................................. 399/61; 399/57
[58] Field of Search ................................. 399/57, 58, 61, 399/62, 65, 30, 237

[56] References Cited

U.S. PATENT DOCUMENTS

| | | | |
|---|---|---|---|
| 5,243,391 | 9/1993 | Williams et al. | 399/57 X |
| 5,447,056 | 9/1995 | Foote | 399/57 X |
| 5,465,619 | 11/1995 | Sotack et al. | 399/61 X |
| 5,724,629 | 3/1998 | Iino et al. | 399/57 |

FOREIGN PATENT DOCUMENTS

| | | |
|---|---|---|
| 55-59475 | 5/1980 | Japan . |
| 56-39570 | 4/1981 | Japan . |
| 63-5751 | 2/1988 | Japan . |
| 63-303380 | 12/1988 | Japan . |
| 1-179064 | 7/1989 | Japan . |
| 3-295453 | 12/1991 | Japan . |

*Primary Examiner*—Sandra Brase
*Attorney, Agent, or Firm*—Ostrolenk, Faber, Gerb & Soffen, LLP

[57] ABSTRACT

In order to detect a toner density in a liquid developer accurately while lowering the influence of ions on the liquid developer, the toner density detecting apparatus 11 detects a toner density in a liquid developer obtained by mixing charged toner particles in a carrier solution. The first and second electrodes 12 and 13 are opposed to each other with a liquid developer therebetween and connected to the first DC power source ($V_1$) thereby to apply the first electrical field to the liquid developer. The toner density detecting apparatus 11 further includes the third and fourth electrodes 14 and 15 opposed to each other in the direction orthogonal approximately to the direction in which the first and second electrodes 12 and 13 are opposed to each other and connected to the second power sources ($V_2$, $V_3$, $V_4$) thereby to apply the second electrical field. The third electrode 14 is divided into plural sub-electrodes 14a and 14b, and the toner density detecting apparatus 11 further includes circuits ($A_1$, $A_2$) for detecting the current values of the sub-electrodes 14a and 14b.

10 Claims, 4 Drawing Sheets

APPARATUS AND METHOD FOR DETECTING TONER DENSITY IN A LIQUID DEVELOPER

BACKGROUND OF THE INVENTION

1. Field of the Invention

The present invention relates to an apparatus and a method for detecting a toner density, more particularly, to an apparatus and a method for detecting a toner density in a liquid developer obtained by mixing charged toner particles in a carrier solution.

2. Description of the Related Art

There is a related art image forming apparatus that has adopted the wet type developing method for feeding a developer onto the peripheral surface of a photosensitive drum that is bearing a static latent image thereby to visualize the static latent image. In this type image forming apparatus, the image quality is affected by the toner density and the toner charging state in the liquid developer, which are varied according to the consumption of toner particles. Consequently, it is indispensable to know the toner density and the toner charging state in the liquid developer and keep the toner particles in a stable state for such an image forming apparatus. A technology for detecting the toner density and the toner charging state such way is thus very important.

There have been made various propositions concerning the above technology so far. For example, the official report of Unexamined Published Japanese Patent Application Laid-Open No. 3-295453 (Issued on Dec. 26, 1991) discloses an evaluation method for a liquid developer used for electrophotography, which detects a charging volume of toner particles by measuring the conductance of an object liquid developer. And, the official report of Unexamined Published Japanese Patent Application Laid-Open No. 63-303380 (Issued on Dec. 9, 1988) discloses a method for controlling a toner density according to a toner feed signal issued corresponding to the inter-electrode conductance of a pair of electrodes disposed in a liquid developer.

Furthermore, the official report of Unexamined Published Japanese Patent Application Laid-Open No. 56-39570 (Issued on Apr. 15, 1981) discloses a method for controlling an image density by measuring the transmittance of a liquid developer using a photosensor and corresponding this measured value to the resistance value of a carrier solution measured using an electrode. And, the official report of Unexamined Published Japanese Patent Application Laid-Oped No. 63-5751 (Issued on Feb. 4, 1988) discloses an apparatus for detecting an effective toner density by combining an electrical field and transmitted light detection. In addition, the official report of Unexamined Published Japanese Patent Application Laid-Open No. 1-179064 (Issued on Jul. 17, 1989) discloses a method for controlling a toner density by measuring the conductance of each color liquid developer used for a common developing apparatus using the same method as that disclosed in the official report of Unexamined Published Japanese Patent Application Laid-Open No. 63-303383.

A liquid developer used for electrophotography is obtained by mixing charged toner particles in a carrier solution. In addition to such charged toner particles, the liquid developer also includes a counter ion and an excess ion generated by a charging control agent (CCA). The counter ion has a reverse polarity of that of charged toner particles. The excess ion usually has the same polarity as that of charged toner particles.

In the case of the evaluation method disclosed in the official report of Unexamined Published Japanese Patent Application Laid-Open No. 3-295453, the electric charge of toner particles is measured by a pair of electrodes thereby to measure the conductance of a liquid developer as a whole; however, a measured charge includes the electric charges of the counter ion and the excess ion. This is why it is difficult to measure only the electric charge of toner particles in a liquid developer. In the case of the toner density controlling method disclosed in the official report of Unexamined Published Japanese Patent Application Laid-Open No. 63-303380, no toner density can be measured. Because, the measured conductance is greatly effected by the counter ion and the excess ion.

In the related art disclosed in each of the official reports of Unexamined Published Japanese Patent Application Laid-Open No. 63-5751 and No. 56-39570, a change of light transmittance is used effectively to detect changes of toner density, thereby the problem arisen in the related art electrical measurement is solved. In this case, however, the following problem will arise from a measurement of light transmittance. In other words, when measuring a light transmittance, it is indispensable to take some measures including those for dipping a pair of photosensors, each being composed of a light emitting element and a light receiving element, in a liquid developer or for disposing a photosensor portion provided with a transparent measuring window that narrows the passage gap through which the liquid developer passes. The method for dipping a pair of photosensors in a liquid developer is confronted with a wiring problem, as well as a contamination problem to be caused by liquid developer particles stuck on the light emitting and/or the light receiving surface. This is why it is difficult to put the method on practical use. The method for measuring using a measuring window will also be confronted with stains on the measuring window, as well as mixing of bubbles and/or foreign matters into the measuring gap, resulting in degradation of the reliability of measurement results. In addition, in the case of the sensing method that uses a transmitted light, it is difficult to obtain stable measurement results, since the transmission level differs between when respective color liquid developers are used and when a black liquid developer is used, as well as among types of liquid developers in use.

The technology disclosed in the official report of Unexamined Published Japanese Patent Application Laid-Open No. 1-179064 measures a conductance by disposing a pair of electrodes just like in the technology disclosed in the official report of Unexamined Published Japanese Patent Application Laid-Open No. 63-303380. Thus, it is impossible to measure the density of charged toner particles.

SUMMARY OF THE INVENTION

Under such the circumstances, it is an object of the present invention to provide an apparatus and a method for detecting a toner density in a liquid developer accurately while lowering the influence of ions on the developer.

In order to achieve the above object, the toner density detecting apparatus of the present invention, which detects a toner density in a liquid developer obtained by mixing charged toner particles in a carrier solution, includes the detecting electrode unit and the density detecting circuit. The electrode unit has the first and second electrodes opposed to each other with a liquid developer therebetween, and the third and fourth electrodes opposed to each other in the direction orthogonal approximately to the direction in which the first and second electrodes are opposed to each other.

The first and second electrodes are connected to a first DC power source thereby to apply the first electrical field to the liquid developer.

The third electrode is divided into plural sub-electrodes and a second electrical field is applied by a second power source between the third and firth electrodes.

The density detecting circuit detects the toner density of the liquid developer by detecting current values of each of the sub-electrodes.

The toner density detecting apparatus of the present invention can apply electrical fields to the liquid developer in two directions orthogonal approximately to each other. Thus, the toner particles, the counter ion, and the excess ion contained in the liquid developer can be moved respectively due to an electrical migration phenomenon according to the mass and charging state of each of the toner particles, the counter ion, and the excess ion. And, since the toner particles are moved faster than the excess ion in the liquid developer due to a mass difference between them, the plural sub-electrodes of the third electrode can suck the excess ion and the toner particles at a different ratio from each other. Consequently, the current value is changed in each of those sub-electrodes. The toner density in the liquid developer can thus be computed by detecting each of those current values. Consequently, it becomes possible to measure a toner density in a liquid developer accurately while lowering the influence of ions on the liquid developer.

The density detecting circuit of the present invention should preferably be provided with a circuit for computing the toner density in the liquid developer by comparing the difference among those measured current values with a preset reference value. Otherwise, instead of such the circuit, the apparatus should preferably be provided with a circuit for computing a toner density in a liquid developer by computing the slope of each current flowing in each of the plural sub-electrodes and comparing the slope with a preset reference value. With any of the above configurations, a toner density can be computed easily according to the measured current values of the plural sub-electrodes of the third electrode.

Furthermore, the second power source should preferably be provided with two DC power sources connected to the third and fourth electrodes selectively while their polarities are reversed to each other. In this case, after a toner density is detected, it is possible to have each of the third and fourth electrodes set in the reverse polarity from the polarity set when a toner density was detected thereby to remove the excess ion and the toner particles from the plural sub-electrodes.

Furthermore, the second power source should preferably be an AC power source obtained by superposing DC voltages. In this case, when compared with a case in which an electrical field is generated only with a DC power source, the toner density detecting accuracy can be more improved.

Another object of the present invention is to provide a method for detecting a toner density in a liquid developer obtained by mixing charged toner particles in a carrier solution, wherein the first and second electrodes are opposed to each other with a liquid developer therebetween and connected to the first DC power source thereby to apply the first electrical field to the liquid developer, the third electrode divided into plural sub-electrodes and at least one of the fourth electrodes are opposed to each other in the direction orthogonal approximately to the direction in which the first and second electrodes are opposed to each other and connected to the second power source so as to apply the second electrical field orthogonal approximately to the first electrical field to the liquid developer, and the current value of each of the sub-electrodes of the third electrode is detected.

According to the toner density detecting method of the present invention, the plural sub-electrodes of the third electrode can suck the excess ion and the toner particles in a liquid developer at a different ratio from each other. Thus, a toner density in a liquid developer can be computed by detecting the current value of each of those sub-electrodes.

DETAILED DESCRIPTION OF THE PREFERRED EMBODIMENTS

Figure 1:
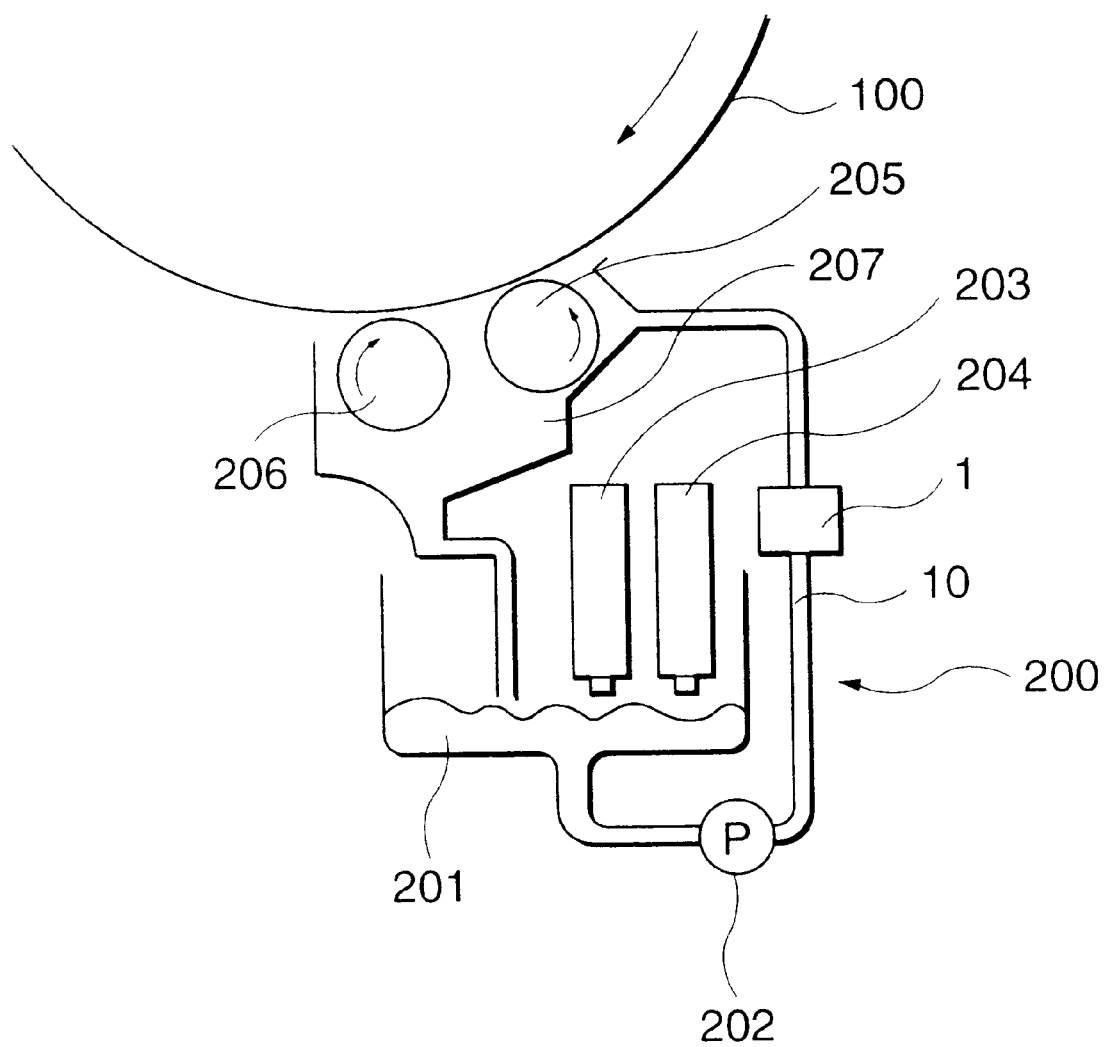
FIG. 1 is a fragmentary side view of an image forming apparatus using a toner density detecting apparatus of the embodiment according to the present invention.

FIG. 1 is a fragmentary side view of an image forming apparatus of the embodiment of the present invention. In FIG. 1, The image forming apparatus uses a photosensitive drum 100. A developing unit 200 for forming a developing pattern image on the photosensitive drum 100 is disposed around the photosensitive drum 100. The developing unit 200 has a housing 201 for storing a liquid developer, pump 202, toner tank 203, carrier solution tank 204, developing roller 205, stirring roller 206, and a detecting electrode element 1. The developing roller 205 and stirring roller 206 is disposed in a developing housing 207.

In this embodiment, positively charged toner particles contained in a carrier solution are used as the liquid developer for an image forming apparatus of the wet type developing method. The toner tank 203 supplies the toner particles to the housing 201 and the carrier solution tank 204 supplies the carrier solution. Usually, a stirring member for stirring the toner particles and the carrier solution is used in the housing 201 to produce the liquid developer.

The pump 202 supplies the liquid developer to the developing housing 207 through a communicating passage 10. The developing roller 205 supplies the liquid developer to the surface of the photosensitive drum 100. The surface has an electrostatic latent image formed by a exposing devise (not shown), and the liquid developer is formed according to the latent image. The stirring roller 206 stirs the liquid developer in the developing housing 207.

Figure 2:
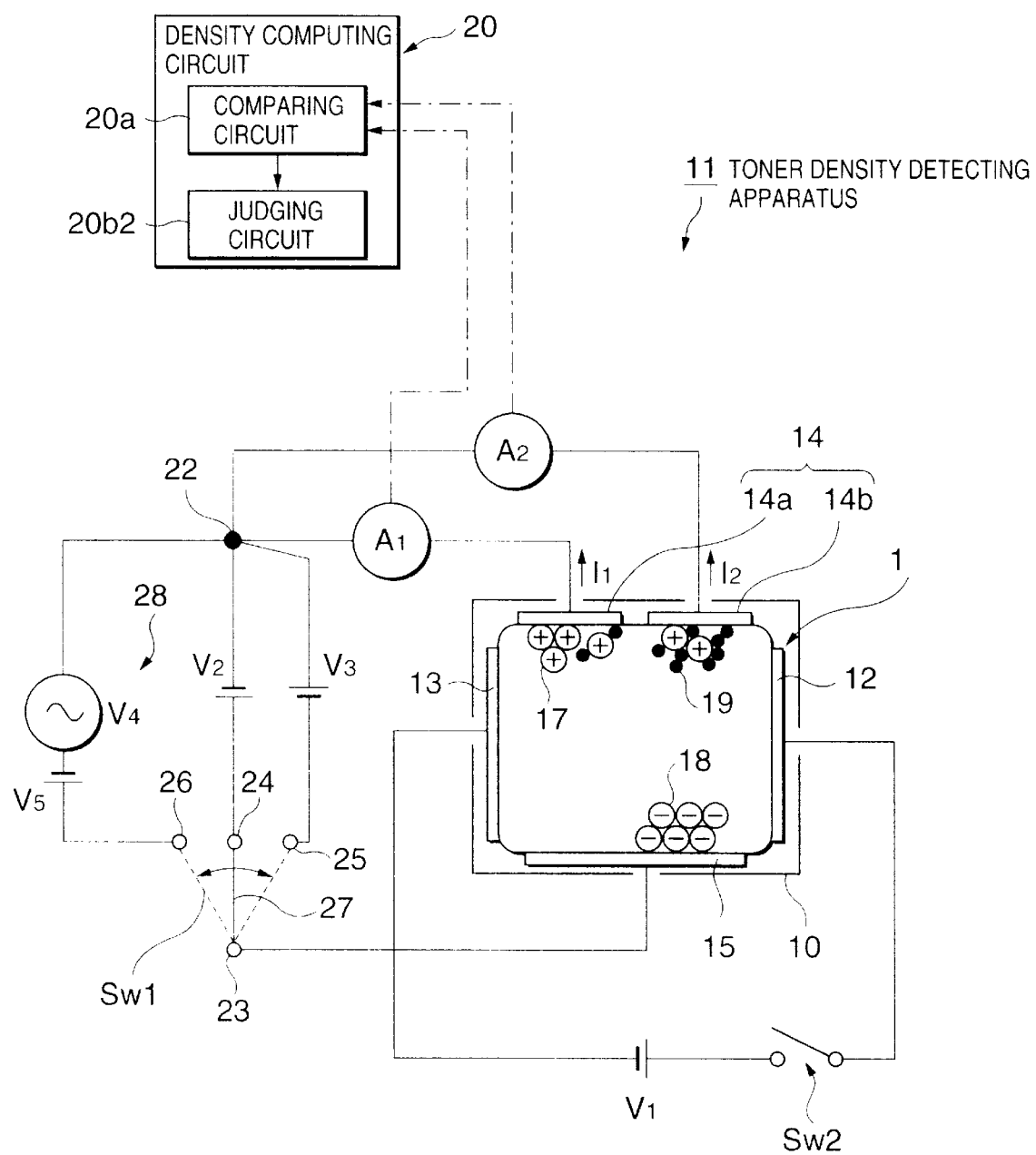
FIG. 2 is a typical view of the toner density detecting apparatus used in the image forming apparatus of FIG. 1.

The detecting electrode unit 1 for detecting toner density in the liquid developer is located in the communicating passage 10 between the pump 202 and the developing housing 207. FIG. 2 is a typical view of a toner density detecting apparatus in the embodiment of the present invention.

In the toner density detecting apparatus 11, the detecting electrode unit 1 is used for a sensor for detecting a toner density in the liquid developer supplied from the pump 202 (FIG. 1). The toner density detecting apparatus 11 includes the detecting electrode unit 1 and a density computing circuit 20.

The detecting electrode unit 1 are composed of the first electrode 12 and the second electrode 13 disposed so as to be opposed to each other with the liquid developer therebetween and connected to a DC power source $V_1$, which is the first power source used to apply a first electrical field to the liquid developer. Between the first electrode 12 and the DC power source $V_1$, is inserted a select switch $SW_2$ used to select the state of the electrical supply to the first and second electrodes 12 and 13. When the select switch $SW_2$ is turned on, the first electrode 12 receives a positive voltage and the second electrode 13 receives a negative voltage.

The detecting electrode unit 1 also includes third and fourth electrodes 14 and 15 disposed so as to be orthogonal approximately to the direction in which the first and second electrodes 12 and 13 are opposed to each other and connected to the second power source 28 thereby to apply a second electrical field orthogonal approximately to the first electrical field to the liquid developer. The third electrode 14 is composed of a sub-electrode 14a disposed at the side of the second electrode 13 and a sub-electrode 14b disposed at the side of the first electrode 12, which are divided and insulated from each other. The second power source 28 includes DC power sources $V_2$ and $V_3$, as well as an AC power source $V_4$ for which DC voltage is superposed. One end of each of the DC power sources $V_2$ and $V_3$ is connected to a junction point 22 commonly with others and the other end is connected to each of the select terminals 24, 25, and 26 of the select switch $SW_1$. One end of the AC power source $V_4$ for which DC voltage is superposed is connected to the junction point 22 and the other end of the SC power source $V_4$ is connected to the select terminal 26 through a DC power source $V_5$. This DC power source faces its negative side to the AC power source $V_4$ and its positive side to the select terminal 26. Between the junction point 22 and the electrode 14a and between the junction point 22 and the electrode 14b are inserted the first ammeter $A_1$ and the second ammeter $A_2$ used as a current detecting means respectively.

Consequently, when the contactor 27 of the select switch $SW_1$ is switched to any of the select terminals 24, 25, and 26, the DC power source $V_2$, the DC power source $V_3$, or the AC power source $V_4$ for which the DC power source is superposed is connected to the sub-electrodes 14a and 14b respectively. When the DC power source $V_2$ is connected, both electrodes 14a and 14b are applied a negative voltage and the fourth electrode 15 is applied a positive voltage, thereby the second electrical field is generated between the third and fourth electrodes 14 and 15. On the other hand, when the DC power source $V_3$ is connected, both sub-electrodes 14a and 15b are applied a positive voltage respectively and the fourth electrode 15 is applied a negative voltage, thereby a third electrical field of DC is generated between the third and fourth electrodes 14 and 15. The direction of the third electrical field is opposite to the direction of the second electrical field. When the AC power source $V_4$ for which DC voltage is superposed is connected, an alternation of electrical fields is generated between the third and fourth electrodes 14 and 15.

The first and second ammeters $A_1$ and $A_2$ function as a DC ammeter respectively when the DC power source $V_2$ or $V_3$ is connected to them. When those ammeters $A_1$ and $A_2$ are connected to the AC power source $V_4$, they function as an AC ammeter respectively. The relationship of the voltage values in both DC power sources $V_1$ and $V_2$ become $V_1 < V_2$ at this time. A reference numeral 19 in FIG. 2 indicates toner particles charged positively and 17 indicates an excess ion whose polarity is the same as that of the toner particles. 18 indicates a counter ion whose polarity is reverse to that of the toner particles.

The toner density computing circuit 20 receives the current value $I_1$ of the electrode 14a measured by the first ammeter $A_1$ and the current value $I_2$ of the electrode 14b measured by the second ammeter $A_2$ thereby to detect a toner density in a liquid developer. The toner density computing circuit 20 includes a comparing circuit 20a and a judging circuit 20b. The comparing circuit 20a has table data obtained by making a preset reference current value proportional to each toner density and computes $I_1 - I_2$, which is a difference between entered current values $I_1$ and $I_2$, then compare this difference with table data. The judging circuit 20b judges a toner density in an object liquid developer according to the comparison result in the comparing circuit 20a.

Figure 3:
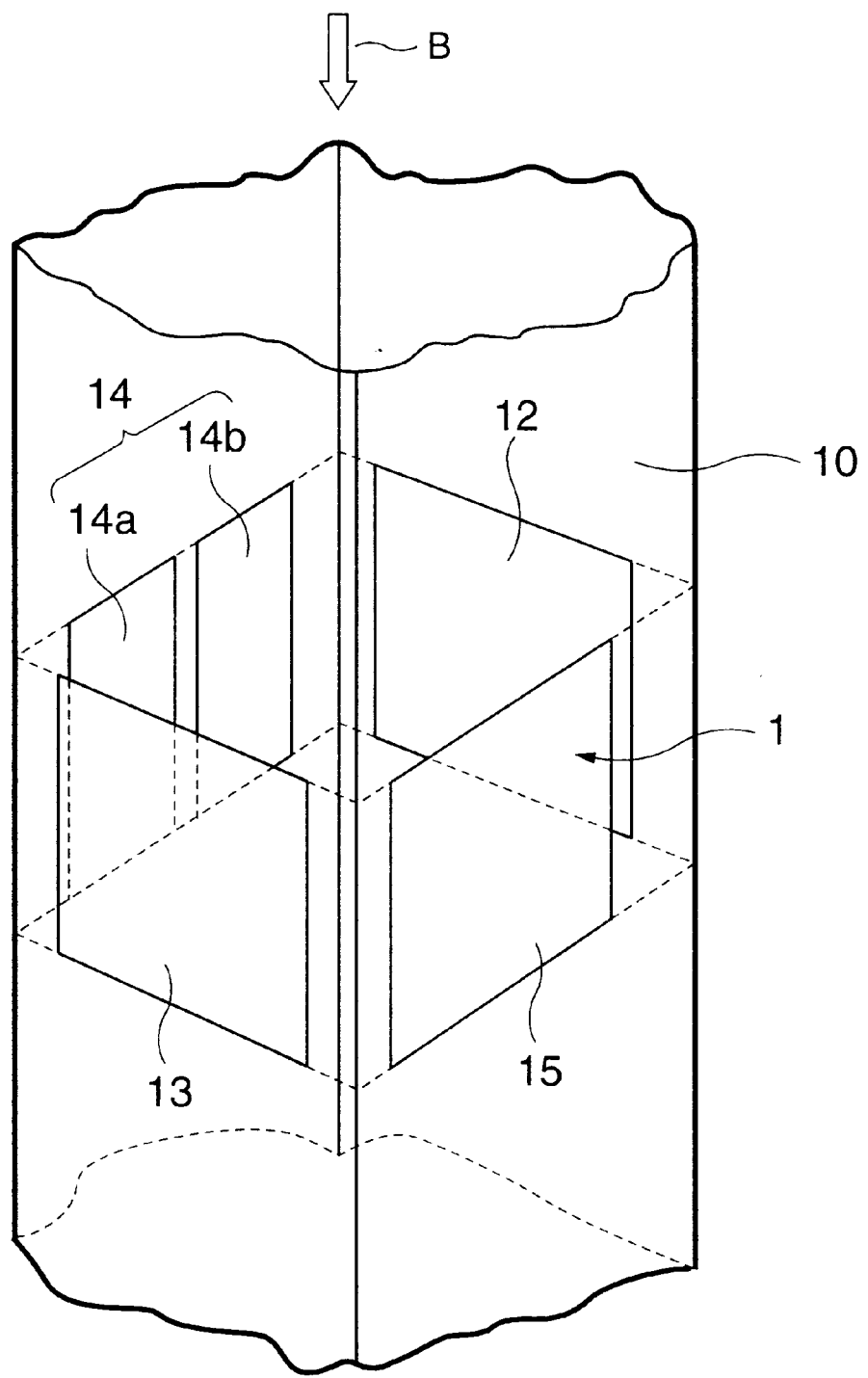
FIG. 3 is a perspective view of a detecting electrode unit of the toner density detecting apparatus shown in FIG. 2.

FIG. 3 is a perspective view of the detecting electrode unit 1 of the toner density detecting apparatus 11. The first to fourth electrodes 12 to 15 in the toner density detecting apparatus 11 are provided in the communicating passage 10 (FIG. 1)

Figure 4:
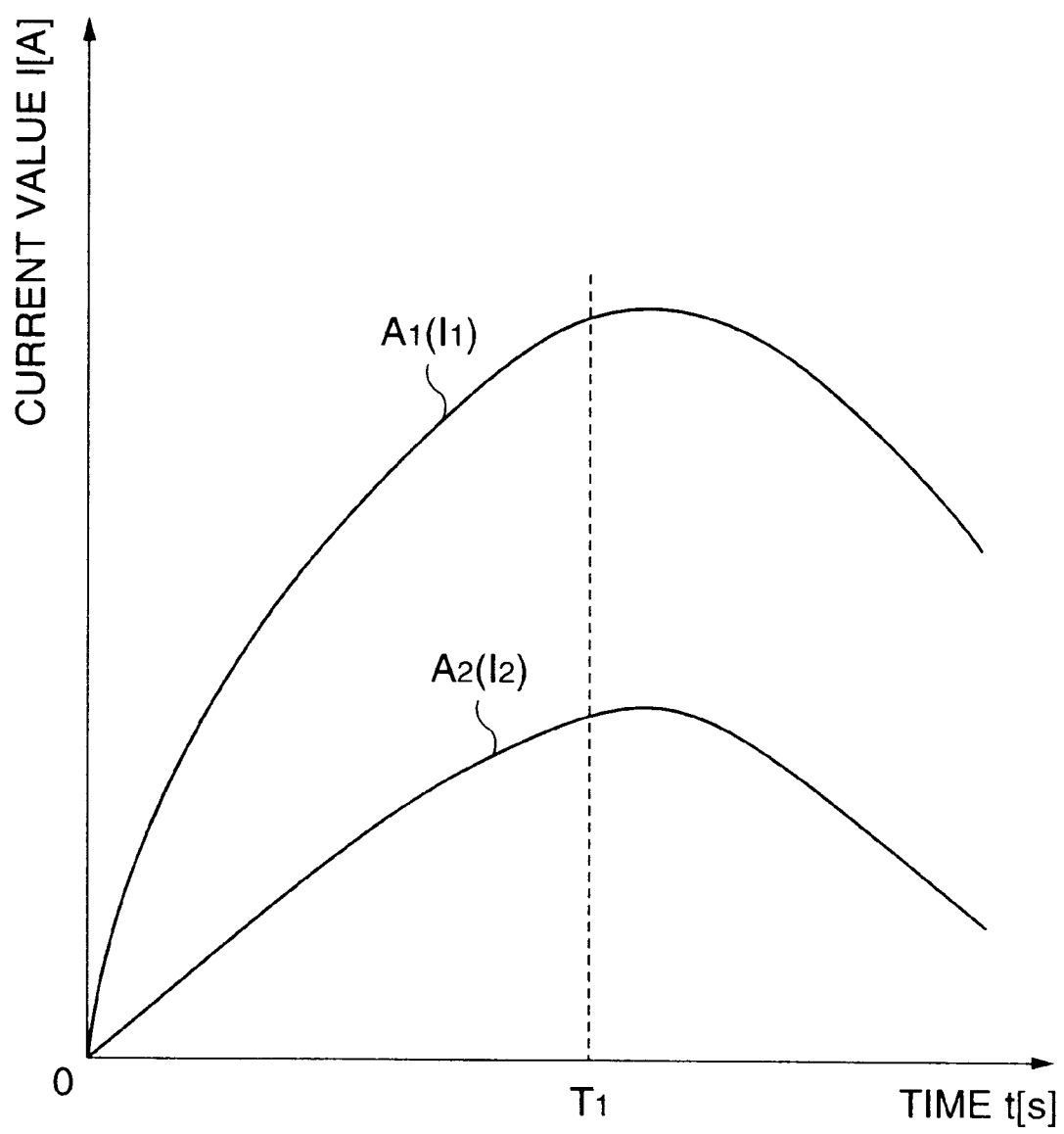
FIG. 4 is a graph indicating the relationship among the current values measured by the toner density detecting apparatus shown in FIG. 2 and the time.

FIG. 4 is a graph indicating the relationship among the current value $I_1$ measured by the first ammeter $A_1$, the current value $I_2$ measured by the second ammeter $A_2$, and the time t. The difference value $I_1 - I_2$ is computed periodically as a sampling operation. This sampling can be executed, for example, between the start of electrical field applying to a liquid developer and the time $T_1$ just before both currents reach their peak values.

Next, an operation of the toner density detecting apparatus 11 will be described. While a liquid developer is fed in the direction of an arrow B (FIG. 3) in the communicating passage 10 toward the developing housing 207 (FIG. 2) from the housing 201 containing the liquid developer, the current value is measured periodically. At first, in FIG. 2, the select switch $SW_2$ is turned on thereby to connect the DC power source $V_1$ to between the first and second electrodes 12 and 13 so that the first electrode enters the positive polarity and the second electrode 13 enters the negative polarity. Consequently, the first electrical field is generated between the first and second electrodes 12 and 13. The select switch $SW_1$ is then changed over thereby to connect the DC power source $V_2$ to between the third and fourth electrodes 14 and 15 so that the third electrode enters the negative polarity and the fourth electrode enters the positive polarity. The second electrical field is thus generated between the third and fourth electrodes 14 and 15. The direction of the second electrical field is orthogonal approximately to the direction of the first electrical field.

While the above electrical field is generated, the excess ion 17 and the toner particles 19 contained in a liquid developer are moved from the first electrode 12 to the second electrode 13 due to an electrical migration phenomenon. During this movement, the excess ion 17 and the toner particles 19 are also driven from the fourth electrode 15 to the third electrode 14. The toner particles 19 moving to the third electrode 14 has a larger mass than the excess ion 17, so that the toner particles 17 driven by an electrical migration phenomenon are slow to move.

Consequently, the excess ion 17 that are faster to move are absorbed on the electrode 14a more than on the electrode 14b. And, toner particles 19 that are slow to move are absorbed on the electrode 14b more than on the electrode 14a. Consequently, the electrical resistance value is increased in both the electrodes 14a and 14b respectively. Since the electrical resistance value is increased more in the electrode 14*b* that sucks toner particles 19 whose mass is large, the current values I$_1$ and I$_2$ are changed as shown in FIG. 4. And, while the above electrical field is generated, the counter ion 18 is moved and absorbed to the fourth electrode 15.

In a predetermined time after an electrical field is applied to the liquid developer, the difference I$_1$–I$_2$ between the current values I$_1$ and I$_2$ is compared with table data in the comparing circuit 20*a* and a toner density in the liquid developer is judged in the judging circuit 20*b* according to the result of comparison in the comparing circuit 20*a*. After this, toner particles are fed into the developer properly according to the result of the toner density judgment.

After a toner density is detected, the select switch SW$_1$ is changed over thereby to connect the DC power source V$_3$ to the third and fourth electrodes 14 and 15. Thus, the third and fourth electrodes 14 and 15 enter the reverse polarity of the polarity set when the toner density was detected. Consequently, the excess ion 17, the toner particles 19, and the counter ion 18 can be removed from the sub-electrodes 14*a*, 14*b*, as well as from the fourth electrode 15. Then, in a predetermined time, the above sampling is executed again.

On the other hand, if the select switch SW$_1$ is switched to the AC power source V$_4$ for which DC voltage is superposed while the first electrical field is generated between the first and second electrodes 12 and 13, an AC electrical field is generated between the third and fourth electrodes 14 and 15. In this case, the electrical field between the third and fourth electrodes 14 and 15 is changed according to the frequency. The excess ion 17 and the toner particles moving to the sub-electrodes 14*a* and 14*b* thus slow down slightly and the density detecting time becomes longer as much. However, since a vibration is applied to the toner particles 19 due to a so-called cycle variability, the toner density detecting accuracy is more improved when compared with a case in which an electrical field is generated only by the DC power source V$_2$. And, when an AC power is supplied, the conductance of the carrier solution in the liquid developer can be measured. Thus, it is possible to detect not only a toner density, but also a state change of the carrier solution.

In the toner density detecting apparatus 11 of the present invention, therefore, electrical fields can be applied to the liquid developer in two directions orthogonal to each other and the toner particles 19 and the excess ion 17 contained in the liquid developer respectively can be moved due to an electrical migration phenomenon according to the mass and charging state of each of the toner particles 19 and the excess ion 17. In addition, while the ion is controlled not to affect the liquid developer, the toner density in the liquid developer can be detected accurately according to the current values of the sub-electrodes 14*a* and 14*b*, which are varied frequently. According to the toner density detecting apparatus 11 composed as described above, therefore, it is possible to solve the problems of the related art toner density detecting apparatus that uses a photosensor to detect a toner density. It is also possible to use the toner density detecting apparatus of the present invention without changing the structure specially when in detecting a toner density in a color liquid developer.

The toner density detecting apparatus 11 of the present invention is simple-structured so that electrodes 12 to 15 are disposed in a portion through which a liquid developer passes. The apparatus 11 is also excellent in durability. In addition, since the first, second, and fourth electrodes 12, 13, and 15 can be formed identically in size and the electrodes 14*a* and 14*b* can be formed identically in size, the manufacturing cost of the toner density detecting apparatus 11 can be reduced. Instead of using the DC power sources V$_1$, V$_2$, and V$_3$, it may also be possible to vary the polarity and the voltage value from a common DC power source as needed. In such a case, it can be expected that the manufacturing cost of the toner density detecting apparatus 11 is reduced more significantly.

In this embodiment, the third electrode 14 is composed of two sub-electrodes 14*a* and 14*b*. However, the configuration of the third electrode 14 is not limited only to that; it may be composed freely. For example, the third electrode 14 may be composed of three or more sub-electrodes disposed in order from the first electrode 12 side to the second electrode 13 side, and divided and insulated from each other. And, since it is only required that the sub-electrodes 14*a* and 14*b* are insulated from each other, they may not be disposed closely to each other as shown in FIG. 1.

In this embodiment, the difference between the current values I$_1$ and I$_2$ is compared with table data thereby to compute a toner density. The present invention is not limited only to the configuration, however. In other words, the present invention may also be provided with a toner density computing circuit 20 composed so as to judge a toner density in the judging circuit 20*b* according to the result of comparison after a slope in changes of both current values I$_1$ and I$_2$ is computed in the comparing circuit 20*a* and the slope is compared with a preset reference value in the comparing circuit 20.

In this embodiment, a toner density is detected for a liquid developer being fed from the housing 201 containing the liquid developer to the developing housing 207. The present invention is not limited only to this configuration, for example, the detecting electrode unit 1 is located in the housing 201 or the developing housing 207, however; a toner density may be detected for the liquid developer stayed in a portion enclosed by the first to fourth electrodes 12 to 15.

In this embodiment, explanation has been made for detecting of a toner density in a liquid developer obtained by mixing positively charged toner particles in a carrier solution, but the present invention is not limited only to such a detecting method. In other words, the method and apparatus of the present invention for detecting a toner density can also detect a toner density in a liquid developer obtained by mixing negatively charged toner particles in a carrier solution.

A preferred embodiment of the present invention is as described above, but the method and apparatus of the present invention for detecting a toner density are not limited only to the embodiment. The present invention also includes methods and apparatuses obtained by modifying and changing the embodiment.

As described above, according to the present invention, since electrical fields are applied to a liquid developer in two directions orthogonal approximately to each other, the toner density in the liquid developer can be measured accurately while controlling ions so as not to affect the developer.

We claim:

1. A toner density detecting apparatus for detecting a toner density in a liquid developer obtained by mixing charged toner particles in a carrier solution, comprising first and second electrodes opposed to each other with a liquid developer therebetween;

a first DC power applying means so as to apply a first electrical field between said first and second electrodes;

third and fourth electrodes opposed to each other in a direction orthogonal approximately to a direction in which said first and second electrodes are opposed to each other, said third electrode being divided into plural sub-electrodes;

a second power applying means so as to apply a second electrical field between said third and fourth electrodes, said second electrical field being orthogonal approximately to said first electrical field; and detecting means for detecting the toner density in the liquid developer by detecting current values of each of said sub-electrodes.

2. A toner density detecting apparatus as defined in claim 1, wherein said detecting means includes current detecting means for detecting a difference of the current values of each of said sub-electrodes, and computing means for computing the toner density in the liquid developer by comparing the difference with a preset reference value.

3. A toner density detecting apparatus as defined in claim 2, wherein said second power applying means includes two DC power sources to be connected to said third and fourth electrodes selectively while their polarities are set reversely to each other.

4. A toner density detecting apparatus as defined in claim 2, wherein said second power applying means includes an AC power source superposed with superposing a DC voltage from a DC power source.

5. A toner density detecting apparatus as defined in claim 1, wherein said current detecting means includes means for computing a toner density in a liquid developer by computing a slope in changes of the value of each current flowing in each of said plural sub-electrodes and comparing said slope with a preset reference value.

6. A toner density detecting apparatus as defined in claim 5, wherein said second power applying means includes two DC power sources to be connected to said third and fourth electrodes selectively while their polarities are set reversely to each other.

7. A toner density detecting apparatus as defined in claim 5, wherein said second power applying means includes an AC power source obtained by superposing a DC voltage.

8. A toner density detecting apparatus as defined in claim 1, wherein said second power power applying means includes two DC power sources to be connected to said third and fourth electrodes selectively while their polarities are set reversely to each other.

9. A toner density detecting apparatus as defined in claim 1, wherein said second power applying means includes an AC power source obtained by superposing a DC voltage from a DC power source.

10. A method for detecting a toner density in a liquid developer obtained by mixing charged toner particles in a carrier solution, comprising the steps of:

providing first and second electrodes which are opposed to each other with a liquid developer therebetween and connected to a first DC power source so as to apply a first electrical field to said liquid developer, providing a third electrode which is divided into plural sub-electrodes and providing a fourth electrode, said third and fourth electrodes being connected to a second power source so as to be opposed to each other in the direction approximately orthogonal to the direction in which said first and second electrodes are opposed to each other, so that a second electrical field between said third and fourth electrodes is applied to said liquid developer, said second electrical field being approximately orthogonal to said first electrical field, and detecting current value of each of said sub-electrodes obtained by dividing said third electrode.

* * * * *